United States Patent [19]
Fahim

[11] Patent Number: 4,937,234
[45] Date of Patent: Jun. 26, 1990

[54] MINERALS IN BIOAVAILABLE FORM

[76] Inventor: Mostafa S. Fahim, 500 Hulen Dr., Columbia, Mo. 65203

[21] Appl. No.: 230,582

[22] Filed: Aug. 10, 1988

[51] Int. Cl.$^5$ .................. A61K 31/715; A61K 31/44; A61K 31/425; A61K 31/40

[52] U.S. Cl. ........................................ 514/53; 514/356; 514/365; 514/423; 514/474; 514/561; 514/563; 514/564; 514/565; 514/865

[58] Field of Search .................. 514/23, 53, 494, 561, 514/423, 563, 564, 565, 365, 356, 474

[56] References Cited

U.S. PATENT DOCUMENTS 4,684,528 8/1987 Godfrey .............................. 514/494

OTHER PUBLICATIONS

Earl Mindell's Vitamin Bible ©1985, pp. 48–52, 70–73 and 109–111.

Primary Examiner—Douglas W. Robinson
Assistant Examiner—Raymond J. Henley, III
Attorney, Agent, or Firm—Grace J. Fishel

[57] ABSTRACT

A soluble mineral in bioavailable form is formed from a mineral salt of a carboxylic acid derivative of a pentose or hexose such as zinc gluconate and an amino acid having the ability of stabilize the mineral salt when the mixture id neutralized in the zone of intracellular pH. Methods of treating an organism with the above-mentioned minerals are disclosed.

13 Claims, No Drawings

MINERALS IN BIOAVAILABLE FORM

BACKGROUND OF THE INVENTION

The present invention relates to minerals in bioavailable form and to methods for the administration thereof to target cells.

Minerals such as zinc, calcium, iron, magnesium, manganese and so forth are involved in certain enzymes and are essential for maintenance of life in man, animals and plants. In some instances, vitamins facilitate the incorporation of the mineral into the enzyme such that enzyme activity is inhibited by a shortage in the mineral or in the vitamin. For example, zinc is involved in the synthesis of DNA by the zinc-containing enzyme DNA polymerase. The vitamin niacin facilitates incorporation of zinc into the peptide subunits of the DNA polymerase enzyme. If either niacin or zinc is deficient in the body, DNA polymerase activity of the tissues may be reduced and the result in both cases is lack of growth.

The principles of drug therapy apply to mineral therapy wherein the goal is to get the appropriate drug into the target tissue in the correct concentration for the sufficient length of time to achieve the desired therapeutic effect. If the concentration of the drug is too low, therapy will be ineffective and if the concentration is too high, toxicity may result.

Because metals are highly charged molecules, many minerals are not absorbed well and do not pass into cells easily even if available in the serum. For example, the prostate is the organ of man that is richest in zinc, and, as substantiated by the latest research, zinc concentration in seminal plasma serves as an indicator for prostate function. Oral administration of a zinc supplement, such as zinc sulfate, zinc chloride or zinc acetate, increases the zinc concentration in the serum but does not consistently increase the zinc concentration in the seminal plasma and improve prostate function.

In addition to difficulties in being absorbed, some minerals are also unpleasant to take. For example, zinc supplements taken orally can produce nausea, vomiting and diarrhea and zinc compounds applied topically are astringent and can cause irritation. Zinc oxide, on the other hand, is neutral and can be applied topically but is not water soluble and is not absorbed into the tissue. The acidity of water soluble zinc salts such as zinc acetate, zinc chloride and zinc sulfate cannot be neutralized with sodium bicarbonate, sodium hydroxide or the like. With sodium bicarbonate, it takes so much of the base, i. e. a molar ratio of 5 to 1, to reach pH 7 that the compound has an elevated sodium content and with sodium hydroxide the neutralized mixture readily precipitates on standing.

In view of the above, there is a need for minerals in bioavailable form which are readily absorbed into the serum whether taken orally, applied topically or injected into the body and which pass readily into the target cells and for suitable methods for the administration thereof. Other objects and features will be in part apparent and in part pointed out hereinafter. The invention accordingly comprises the products and methods hereinafter described and equivalents thereof, the scope of the invention being indicated in the subjoined claims.

SUMMARY OF THE INVENTION

The present invention began with the observation that lysine, arginine and histidine are basic amino acids (positively charged at pH 6) and might be used to neutralize the acidity of zinc salts such as zinc acetate, zinc chloride and zinc sulfate. The experiment, however, does not provide an effective delivery form because the mixture readily precipitates on standing. It has been discovered that zinc gluconate, unlike zinc acetate, zinc chloride and zinc sulfate, can be neutralized with the above-mentioned basic amino acids to provide a stable mixture. It has also been discovered that zinc gluconate, unlike zinc acetate, zinc chloride and zinc sulfate, can be neutralized with a base such as sodium hydroxide in the presence of certain nonpolar amino acids and certain uncharged polar amino acids to provide a water soluble, stable mixture.

Minerals neutralized in accordance with the present invention are absorbed more readily and act more efficiently on the cellular tissue level in the target organ than minerals alone. Surprisingly this is accomplished without compromising the bacterial effect of the zinc which has been thought to be due, at least in part, on the acidity of the zinc salt. This is new knowledge in the field of bacteriology and products based on the subject discoveries can be used in the new born and elderly and in tissue areas that are very sensitive to acidity such as the eyes, nose and irritated vagina where soluble zinc salts have not been used effectively before.

DESCRIPTION OF THE PREFERRED EMBODIMENTS

In accordance with the present invention, a mineral salt of a carboxylic acid derivative of a pentose or hexose such as zinc gluconate or zinc gulonate is neutralized in the presence of certain amino acids to provide minerals in bioavailable form which are absorbed more readily and act more efficiently on the cellular level in the target organ than minerals alone. Other minerals which may be administered in the subject form include calcium, iron, magnesium, manganese and the like.

Zinc gluconate, like zinc acetate, zinc chloride and zinc sulfate, is acidic as illustrated by the following table:

| Solutions | pH of Zinc Solutions pH | |
|---|---|---|
|  | 0.1 M | 0.2 M |
| Zinc acetate | 6.7 | 6.6 |
| Zinc chloride | 6.4 | 6.2 |
| Zinc sulfate | 5.7 | 5.45 |
| Zinc gluconate | 5.85 | 5.65 |

In common with the other soluble zinc salts mentioned above, zinc gluconate cannot be neutralized with sodium hydroxide without precipitating the mixture. It has been discovered, however, that the acidity of the zinc gluconate can be neutralized by adding the following amino acids and adjusting the pH to 7.0: alanine, valine, isoleucine, proline, glycine, serine, threonine, asparagine, glutamine, lysine, arginine, histidine and mixtures thereof. The adjustment cannot be made with cysteine, tyrosine, aspartic acid or glutamic acid.

In general, it is preferred that the mineral salt and the amino acid be present in substantially equimolar amounts. Suitable therapeutic formulations are formed with a molar amount of mineral salt such as zinc gluconate to amino acid from about 0.05M:1.0M to about 1.0M:0.05M, preferably from about 0.1M: 0.3M to 0.3M:0.1M and most preferably from about 0.1M:0.1M to 0.3M:0.3M and neutralized to a pH in the range from about 6.0 to 8.0, preferably from about 6.5 to 7.5 and most preferably 7.0.

The general structural formula for the 20 amino acids commonly found in proteins is R—C(H)(NH2)—COOH and the most meaningful way to classify them is based on the polarity of their R groups: those with (1) nonpolar or hydrophobic R groups, (2) neutral (uncharged) polar R groups, (3) positively charged R groups and (4) negatively charged R groups (at pH 6.0 to 7.0, the zone of intracellular pH). As discussed below, the amino acids suitable for use in accordance with the present invention cut across the classification groups.

There are eight standard amino acids having nonpolar R groups. Five have aliphatic hydrocarbon R groups (alanine, leucine, isoleucine, valine and proline), two with aromatic rings (phenylalanine and tryptophan) and one containing sulfur (methionine). Of these, as shown in the following table, alanine, valine, isoleucine and proline are suitable for use as described herein, whereas leucine, phenylalanine, tryptophan and methionine are not:

| 0.1 M Zinc Gluconate and 0.1 M Amino Acid Solutions | | |
|---|---|---|
| Nonpolar Amino Acids | pH | Observations |
| Alanine | 5.1 | pH adjusted to 7.0 with NaOH does not precipitate |
| Valine | 5.1 | pH adusted to 7.0 with NaOH does not precipitate |
| Leucine | 5.0 | pH adjusted to 7.0 with NaOH precipitates |
| Isoleucine | 5.1 | pH adjusted to 7.0 with NaOH does not precipitate |
| Proline | 5.4 | pH adjusted to 7.0 with NaOH does not precipitate |
| Phenylalanine | 4.9 | pH adjusted to 7.0 with NaOH precipitates |
| Tryptophan | | Not soluble |
| Methionine | 5.1 | pH adjusted to 7.0 with NaOH precipitates |

There are seven standard amino acids with uncharged polar R groups which can hydrogen-bond with water. The polarity of serine, threonine and tyrosine is contributed by their hydroxyl groups; that of asparagine and glutamine by their amide groups and that of cysteine by its sulfhydryl group. Glycine, the borderline member of the group, is sometimes classified as a nonpolar amino acid but its R group, a single hydrogen atom, is too small to influence the high degree of polarity of the amino and carboxyl groups. Asparagine and glutamine are the amides of aspartic acid and glutamic acid and are easily hydrolyzed by acid or base to aspartic acid and glutamic acid, respectively. Cysteine and tyrosine have the most polar substituents of this class of amino acids, namely the thiol and phenolic hydroxyl groups, respectively. These groups tend to lose protons by ionization far more readily than the R groups of other amino acids of this class, although they are only slightly ionized at pH 7.0. Of the above-mentioned amino acids with uncharged polar R groups, as shown in the following table, glycine, serine, threonine, asparagine and glutamine are suitable for use herein, whereas cysteine and tyrosine are not:

| 0.1 M Zinc Gluconate and 0.1 M Amino Acid Solutions | | |
|---|---|---|
| Amino Acids with Uncharged Polar R Groups | pH | Observations |
| Glycine | 5.0 | pH adjusted to 7.0 with NaOH does not precipitate |
| Serine | 4.8 | pH adjusted to 7.0 with NaOH does not precipitate |
| Threonine | 5.0 | pH adjusted to 7.0 with NaOH does not precipitate |
| Cysteine | 4.3 | pH adjusted to 7.0 with NaOH precipitates |
| Tyrosine | | Not soluble |
| Asparagine | 4.8 | pH adjusted to 7.0 with NaOH does not precipitate |
| Glutamine | 5.0 | pH adjusted to 7.0 with NaOH does not precipitate |

The basic amino acids, in which the R groups have a net positive charge at pH 7.0, all have six carbon atoms. They consist of lysine, which bears a positively charged amino group at the e position on its aliphatic chain; arginine, which bears the positively charged guanidinium group and histidine, which contains the weakly basic imidazolium function. Histidine is the only amino acid having buffering capacity near pH 7.0 with a pK' of the R group near 7.0. All of the basic amino acids as shown in the following table are suitable for use in the present invention:

| 0.1 M Zinc Gluconate and 0.1 M Amino Acid Solutions | | |
|---|---|---|
| Amino Acids with (−) Charged Polar Groups | pH | Observations |
| Lysine | 7.4 | pH adjusted to 7.0 with HCl does not precipitate |
| Arginine | 7.4 | pH adjusted to 7.0 with HCl does not precipitate |
| Histidine | 5.5 | pH adjusted to 7.0 with NaOH does not precipitate |

The two amino acids with negatively charged (acidic) R groups are aspartic acid and glutamic acid, each with a second carboxyl group which is fully ionized and negatively charged at pH 6 to 7. Neither of these amino acids is suitable for use as herein described as shown in the following table:

| 0.1 M Zinc Gluconate and 0.1 M Amino Acid Solutions | | |
|---|---|---|
| Amino Acids with (+) Charged Polar Groups | pH | Observations |
| Aspartic acid | | Not soluble |
| Glutamic acid | | Not soluble |

In addition to the standard 20 amino acids commonly found in proteins, there are also synthetic and other naturally occurring amino acids known to occur biologically in free or combined form. Among these other amino acids, other suitable amino acids for use herein may be identified if screened as described above.

In some instances, it is advantageous to administer the neutralized mineral salt in combination with a vitamin such as vitamin C, niacin and so forth depending on the condition to be treated. For example, if the mixture is intended as a food supplement to stimulate growth, niacin is selected, whereas if the mixture is intended to stimulate wound healing, vitamin C is chosen. Minerals in accordance with the present invention, optionally in combination with other active therapeutic ingredients such as vitamins and other drugs, are utilized in aqueous, emulsion or dried form in combination with other materials such as glycerin, carboxy methyl cellulose, oils, sweeteners, flavors and so forth as carriers or excipients. Depending on the form and the target tissue to be treated, they are taken orally, applied topically to the external or internal epithelium or injected.

The following examples illustrate the invention.

EXAMPLE 1

Twenty-eight newborn children, ranging from 3 months to 11 months of age, with diaper rash, redness and irritation were sprayed twice daily for three days with the following formula.

| Composition percent by weight |
| --- |
| 1.0% Zinc gluconate |
| 0.3% Lysine |
| 10.0% Glycerin |
| q.s. Distilled water and HCl to adjust pH to 7.0 |

Improvement was seen in all cases and fifty percent of the patients showed improvement by the second day.

EXAMPLE 2

Thirty-six pigs in confinement on a farm had wet wounds. Some of the pigs had wounds on the ears, due to biting and fighting, and some had wounds on the ears due to scratches with wire. The wounds had been previously treated with sulfa drug for wound healing but the wound did not heal and continued to exist.

The wounds were sprayed twice daily for two days with the following formula:

| Composition percent by weight |
| --- |
| 5.0% Zinc gluconate |
| 1.5% Lysine |
| 10.0% Glycerin |
| q.s. Distilled water and HCL to adjust pH to 7.0 |

Within two days, the ulceration began to heal, the bleeding stopped, and the condition improved. The ulceration was no longer visible after two weeks, and the skin returned to normal within one month.

EXAMPLE 3

The irritated skin of the thighs and buttocks of one 6-month old baby and three children, aged 2 to 2½ years, were treated with the following formula:

| Composition percent by weight |
| --- |
| 1.0% Zinc gluconate |
| 0.3% Lysine |
| q.s. Lotion manufacture by L. T. York, Brookfield, Missouri, consisting of an emulsified hydrogenated mixture of olive, palm and coconut oils and HCl to adjust pH to 7.0. |

The irritation, redness and completely vanished in five days.

EXAMPLE 4

Seven diabetic patients with cornification of the heel and dryness of the feet were sprayed with the same formula as that used for treating diaper rash in Example 1. The lotion was applied overnight and this regimen was followed for one week. After one week, the dryness, scaling and odor of the feet had vanished and the skin was softened.

EXAMPLE 5

Seventeen patients were asked to spray the inside of their shoes with a formulation consisting of 5.0% zinc gluconate, 1.5% lysine percent by weight and q.s. water and HCl to adjust pH to 7.0. Swabs taken before the shoes were sprayed evidenced heavy growth of bacteria while swabs taken 8 hours later evidenced scant growth. The spray decreased both the odor and bacteria in the shoes.

EXAMPLE 6

A gel containing the following was applied twice daily for five days to three dogs with hot spot, scales, dry skin, hair loss and pathological documentation of tinea vulgaris on the skin.

| Composition percent by weight |
| --- |
| 2.0% Carboxy methyl cellulose |
| 5.0% Zinc gluconate |
| 1.5% Lysine |
| q.s Water and HCl to adjust pH to 7.0 |

After five days, the redness and scales had vanished and, within two weeks, hair growth had resumed. One of the dogs had Demodex mites under the skin and was treated with the gel for ten days. The gel inhibited the growth of the mites and the hair resumed growth.

EXAMPLE 7

Four dogs experienced recurrence of chronic dermatitis during the course of six to 18 months despite treatment with different antibiotics and cortisones. Dermatitis in dogs occurs as a result of allergic reaction which is not fully understood.

The following formulation was added once daily to the drinking water of each dog on the basis of one ml of the solution per one kilogram of body weight.

| Composition percent by weight |
| --- |
| 1.0% Zinc gluconate |
| 5.0% Potassium gluconate |
| 0.5% Lysine |
| 2.0% Taurine |
| q.s. Beef flavored water and HCl to adjust pH to 7.0 |

Each ml of the solution contained one mg of zinc gluconate and 4 mg of potassium gluconate, 0.5 mg of lysine and 2 mg of taurine.

After two weeks of this regimen, the dry and scaly skin of all four dogs showed improvement and the hair coat appeared healthier. By the end of one month, there was no evidence of dermatitis whatsoever. During the three month follow-up period to date, the dermatitis has not recurred although episodes of dermatitis generally increase during hot and dry weather characteristic of the last two months of the follow-up period (June and July 1988). None of the dogs exhibited signs of toxicity, stomach irritation, diarrhea or vomiting due to ingestion of zinc gluconate at the recommended dose based on body weight.

EXAMPLE 8

During the months of June and July 1988, characterized by drought conditions and extreme heat, many dogs suffered dryness and inflammation of the feet/paws. The following was formulated as a foot ointment or spray for prevention of burning and drying of the feet/paws caused by the extreme conditions:

| Composition percent by weight | |
|---|---|
| 2.0% | Carboxy methyl cellulose |
| 5.0% | Zinc gluconate |
| 1.5% | Lysine |
| 1.5% | Histidine |
| q.s. | Water and HCl to adjust pH to 7.0 |

The ointment was applied to the feet/paws once daily for two months. The dogs were examined daily for signs of discomfort. The condition improved and protection was achieved by the end of the two month period of treatment.

EXAMPLE 9

On a daily basis for two weeks, six dogs with halitosis, one of which also had fungus growth on the tongue, were fed two dog biscuits (20 grams per day) that had been impregnated with the following formula:

| Composition percent by weight | |
|---|---|
| 5.1% | Zinc gluconate |
| 1.55% | Histidine |
| 1.74% | Arginine |
| 1.46% | Lysine |
| q.s. | Water and HCl to adjust pH to 7.0 |

After two weeks, the halitosis had disappeared and the hygienic conditions of the oral cavity improved. The dark spots on the tongue of the one dog that had fungus growth were no longer visible and the tongue resumed its normal appearance.

EXAMPLE 10

Six dogs exhibiting eye problems were divided into the following groups based on diagnosis:
A. Two with inflammation of the lacrimal sac;
B. Three with sub-conjunctival hemorrhage and inflammation of the iris, and
C. One with corneal keratitis and ulcerative inflammation and blepharitis of the eyelids.

The infected eyes of the dogs were treated by applying one ml of the following eye drop formula twice daily for seven days.

| Composition percent by weight | |
|---|---|
| 3.0% | Zinc gluconate |
| 1.0% | Lysine |
| 0.5% | Carboxy methyl cellulose |
| q.s. | Water and HCl to adjust pH to 7.0 |

The eyes of Groups A and B improved in seven days of treatment; however, for Group C, the treatment took 10 days.

EXAMPLE 11

The bleeding gums of two horses and one donkey were sprayed with the following formula having a pH of 7:

| Composition percent by weight | |
|---|---|
| 3.0% | Zinc gluconate |
| 0.3% | Lysine |
| 0.5% | Hydroxyproline |
| 0.28% | Taurine |
| 1.0% | Carboxy methyl cellulose |
| q.s. | Water with sweetener and HCl to adjust pH to 7.0 |

Carboxy methyl cellose was added to enable the solution to adhere to the mucosa of the gums and to prevent physical injury caused by dry food such as hay and barley. Sweetener was added because of horses' preference for it.

The gums of the animals were sprayed twice daily for one week. The bleeding stopped and the bad odor of the oral cavity was eliminated. Tenderness of the gums, when touched, diminished. The owners were advised to spray the gums of the animals once or twice weekly as a preventative measure.

EXAMPLE 12

Eight patients, who had suffered from athlete's foot for a period of 2–3 years and who had tired Dr. Scholl's products and different soak solutions, such as dried saponaria soak, were subjects in the study. Microscopic examination and fungal culture of a sample taken from each patient identified the pathogen as Trichophyton mentagrophytes.

The patients were advised to spray the feet and the shoes twice daily, once in the morning and once in the evening, with the following formula:

| Composition percent by weight | |
|---|---|
| 2.0% | Zinc ascorbate* |
| 2.0% | Zinc gluconate |
| 1.0% | Lysine |
| 0.5% | Carboxy methyl cellulose |
| q.s. | Water and HCl to adjust pH to 7.0 |

*Preparation of zinc ascorbate is described in Example 13 below.

The treatment regimen for athlete's foot showed positive effects after three days, including elimination of itching of the feet and decreased odor of the shoes. After five to seven days of treatment, the feet were normal.

As a preventative measure, the patients were advised to apply the spray twice weekly. During a 5½ months follow up period, to date, none of the patients experienced a recurrence of athlete's foot.

EXAMPLE 13

Thirty-five g of ascorbic acid (2M) is dissolved in 150 ml water and cooled to 4 C. The initial pH of the solution was 2. Eight g of zinc oxide (1M) was added while the solution was continuously stirred and kept cool. After a few hours, all of the zinc oxide went into solution and pH rose to 4.9. The mixture which was light yellow in color was immediately frozen and dried under vacuum. This yielded a very light yellow colored powder with a molecular weight of 415.61. The dry powder was stable, while solutions neutralized with sodium hydroxide to pH 7 were not.

EXAMPLE 14

A formulation in powder form containing zinc and lysine which when dissolved in water forms a neutral solution was prepared as follows:

Two M lysine and 1M zinc gluconate was dissolved in water to form a solution having a pH 7.4 and was neutralized to pH 7 with HC1. After the zinc and amino solution was neutralized, it was frozen immediately in liquid nitrogen. The frozen solution was then lyophilized for 24 hours to remove water. When dried, a white powder was formed containing zinc and amino acid, which when dissolved in water forms a neutral solution (pH 7).

Comparable formulations were formed with arginine and histidine but in the case of histidine the solution is neutralized with NaOH because the solution has a pH of 5.5.

EXAMPLE 15

Two patients with vaginitis were treated twice a day for 3 days with a solution consisting of 3% zinc gluconate, 1% lysine, 1% carboxy methyl cellulose and q. s. water and HCl to adjust the pH to 7.0. The burning sensation ceased 24 hours after treatment and the inflammation decreased and the tenderness and pain diminished.

EXAMPLE 16

Three middle aged female patients were treated with the composition described in Example 3 as a face cream. Each patient was instructed to apply the cream once or twice daily. Within three weeks, all showed improved skin condition including some wrinkle effacement and none experienced irritation or other adverse side effect.

EXAMPLE 17

A formulation having a pH of 7.1 formed from 0.1M zinc gluconate solubilized with 0.1M lysine in water was added to Difco Tryptic Soy Broth (TSB). This yielded a solution with very slight turbidity and a pH of 6.87. The pH was raised to 7.2 with 1M NaOH, requiring about 1.2 ml per 50 ml of solution. This neutralized solution, designated ZTSB was filter sterilized using a 0.2 micron filter. Approximately 15 ml of ZTSB would pass through a filter before it became clogged. There was no visible amount of material on the surface of the filter indicating that very little zinc was lost during the sterilization process. Control TSB was sterilized in the same manner.

SPECTROPHOTOMETRIC STUDIES

Four strains of bacteria were utilized: *E. coli* ATCC 25922, *Pseudomonas aeruginosa* ATCC 27853, *Staphylococcus aureus* ATCC 25923 and *Streptococcus fecalis* ATCC 33186. These are strains used in quality control evaluation of antibiotic disc susceptibility testing. All four strains were allowed to grow overnight in TSB. 250 ul of each culture was placed in wells of Dynatech Immulon I ELISA 96 well microtiter plates. The absorbance of each was determined using an automated plate reader attached to a microcomputer. Readings at 560, 595 and 650 nm were made blanking against 250 ul of distilled water. The wavelength of 560 nm showed the greatest sensitivity and was chosen for further studies. Sterile TSB and ZTSB were also included; their absorbance at these wavelengths were negligible compared to the blank.

PRELIMINARY EVALUATION OF ZTSB

Sterile tubes of TSB and ZTSB containing 1.0 ml of media were each inoculated with identical amounts of each of the above four strains and incubated overnight at 35 C in air. Uninoculated control tubes of both media were included. After incubation, there was slight turbidity in each of the ZTSB tubes including the control tube. The degree of turbidity was indistinguishable between these ZTSB tubes. The control TSB tube was clear, while all inoculated TSB tubes showed heavy turbidity indicative of bacterial growth. These results indicated that bacterial growth was inhibited in ZTSB, but there was some chemical precipitation under incubation. Prolonged storage of sterile ZTSB at 4C also yielded a slight amount of precipitation.

SPECTROPHOTOMETRIC EVALUATION OF BACTERIAL GROWTH IN ZTSB

Each of the above four bacterial strains were grown overnight at 35C in TSB. Tubes of ZTSB and control TSB each containing 5.0 ml of broth were inoculated with 10 ul of culture from each of the four bacterial strains. Uninoculated control tubes were included. After 0, 1, 3, 4, 5, 6, 7, 8 and 24 hours of incubation at 35C in air, 250 ul aliquots from each test and control tube were placed in wells of a microtiter plate. The absorbance at 560 nm was determined; a distilled water blank was used with each reading interval. The results are given in the following table:

| | | | | Absorbance at 560 nm | | | | | | | |
|---|---|---|---|---|---|---|---|---|---|---|---|
| | | TSB | ZTSB | TSB | | | | ZTSB | | | |
| Hour | dH$_2$O | con. | con. | Ec* | Ps | Sa | Sf | Ec | Ps | Sa | Sf |
| 0 | .000 | .014 | .057 | .016 | .020 | .016 | .015 | .060 | .071 | .050 | .058 |
| 1 | .000 | .014 | .069 | .021 | .024 | .017 | .014 | .065 | .074 | .054 | .049 |
| 3 | .000 | .013 | .071 | .100 | .040 | .028 | .021 | .066 | .075 | .056 | .050 |
| 4 | .000 | .015 | .081 | .215 | .053 | .049 | .039 | .076 | .087 | .065 | .060 |
| 5 | .000 | .014 | .090 | .437 | .064 | .081 | .085 | .087 | .097 | .074 | .067 |
| 6 | .000 | .012 | .094 | .559 | .077 | .126 | .179 | .089 | .098 | .073 | .070 |
| 7 | .000 | .013 | .099 | .646 | .101 | .209 | .330 | .092 | .102 | .079 | .073 |
| 8 | .000 | .014 | .110 | .663 | .132 | .330 | .444 | .103 | .113 | .086 | .080 |
| 24 | .000 | .013 | .287 | .692 | .993 | .690 | .487 | .271 | .282 | .277 | .276 |

Ec = *E. coli* 25922
Ps = *Pseudomonas aeruginosa* 27853
Sa = *Staph. aureus* 25923
Sf + *Strep. fecalis* 33186

Additionally, after 24 hours of incubation, the contents of each inoculated TSB and ZTSB tube was streaked for isolation on 5% sheep blood agar and incubated overnight. There were viable bacteria in all inoculated tubes except ZTSB Ec and ZTSB ps. This data along with the data showing no detectable viable bacteria in the Ec and Ps ZTSB tubes implies that ZTSB not only inhibited the growth of *E. coli* and *Pseudomonas aeruoinosa*, but also was bactericidal under the incubation conditions.

In view of the above, it will be seen that the several objects of the invention are achieved and other advantageous results attained. As various changes could be made in the above without departing from the scope of the invention, it is intended that all matter contained in the above description shall be interpreted as illustrative and not in a limiting sense.

What is claimed:

1. A pharmaceutically acceptable, bioavailable composition having a pH in the range from about 6 to 8 comprising a solution of a mineral gluconate salt and an amino acid capable of forming the solution, said mineral gluconate salt and amino acid being present in substantially equal molar amounts and at a concentration in the range from about 0.05M to 1.0M.

2. The composition of claim 1 wherein the amino acid is selected from the group consisting of alanine, valine, isoleuciine, proline, glycine, serine, threonine, asparagine, glutamine, lysine, arginine, histidine and mixtures thereof.

3. The composition of claim 2 having a pH in the range from about 6.5 to 7.5 wherein the mineral gluconate salt is zinc gluconate and the zinc gluconate and amino acid are present at a concentration in the range from about 0.1M to 0.3M.

4. The composition of claim 3 having a pH of 7.0.

5. A pharmaceutically acceptable, bioavailable composition having a pH of substantially 7.0 comprising zinc gluconate and an amino acid selected from the group consisting of alanine, valine, isoleucine, proline, glycine, serine, threonine, asparagine, lysine, arginine, histidine and mixtures thereof said zinc gluconate and amino acid being present in substantially equal molar amounts and at a concentration in the range from about 0.1M to 0.3M.

6. The composition of claim 5 wherein the amino acid is lysine.

7. The composition of claim 5 additionally comprising a vitamin soluble in said composition in an effective amount for treating a vitamin deficiency.

8. The composition of claim 7 wherein the vitamin in niacin in an effective amount for treating a niacin deficiency.

9. The composition of claim 7 wherein the vitamin is vitamin C in an effective amount for treating vitamin C deficiency.

10. A method of treating a living organism having a condition responsive to treatment with minerals which comprises administering to said organism a pharmaceutically acceptable, bioavailable composition having a pH of substantially 7.0 in a therapeutically effective amount, said composition comprising a solution of zinc gluconate and an amino acid selected from the group consisting of alanine, valine, isoleucine, proline, glycine, serine, threonine, asparagine, glutamine, lysine, arginine, histidine and mixtures thereof, said zinc gluconate and amino acid being present in substantially equal molar amounts an at a concentration in the range from about 0.1M to 0.3M.

11. A method of treating diaper rash which comprises topically applying a pharmaceutically acceptable, bioavailable composition having a pH of substantially 7.0 to a patient in need of treatment for diaper rash in a therapeutically effective amount, said composition comprising a solution of zinc gluconate and an amino acid selected from tube group consisting of alanine, valine, isoleucine, proline, glycine, serine, threonine, asparagine, glutamine, lysine, arginine, histidine and mixtures thereof, said zinc gluconate and amino acid being present in substantially equal molar amounts and at a concentration in the range from about 0.1M to 0.2M.

12. A method of treating vaginitis which comprises applying a pharmaceutically acceptable, bioavailable composition having a pH of substantially 7.0 to a patient in need of treatment for vaginitis in a therapeutically effective amount, said composition comprising a solution of zinc gluconate and an amino acid selected from the group consisting of alanine, valine, isoleucine, proline, glycine, serine, threonine, asparagine, glutamine, lysine, arginine, histidine and mixtures thereof, said zinc gluconate and amino acid being present in substantially equal molar amounts and at a concentration in the range from about 0.1M to 0.2M.

13. A method of treating skin dryness which comprises topically applying a pharmaceutically acceptable, bioavailable composition having a pH of substantially 7.0 to a patient in need of treatment for skin dryness in a therapeutically effective amount, said composition comprising a solution of zinc gluconate and an amino acid selected from the group consisting of alanine, valine, isoleucine, proline, glycine, serine, threonine, asparagine, glutamine, lysine, arginine, histidine and mixtures thereof, said zinc gluconate and amino acid being present in substantially equal molar amounts and at a concentration in the range from about 0.1M to 0.2M.

* * * * *